US00PP12824P2

(12) United States Plant Patent
van Gaalen

(10) Patent No.: US PP12,824 P2
(45) Date of Patent: Aug. 6, 2002

(54) PHLOX PLANT NAMED 'RUBYMINE'

(75) Inventor: Irenaeus Antonius Maria van Gaalen, Den Hoorn (NL)

(73) Assignee: Witteman & Co. 'Multiflora' B.V., Hillegom (NL)

( * ) Notice: Subject to any disclaimer, the term of this patent is extended or adjusted under 35 U.S.C. 154(b) by 11 days.

(21) Appl. No.: 09/840,804

(22) Filed: Apr. 25, 2001

(51) Int. Cl.[7] ..... A01H 5/00
(52) U.S. Cl. ..... Plt./320
(58) Field of Search ..... Plt./320

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Phlox plant named 'Rubymine', characterized by its unique green and pale yellow variegated foliage; upright plant habit; and numerous purple and light pink bi-colored flowers.

2 Drawing Sheets

BACKGROUND OF THE INVENTION

The present Invention relates to a new and distinct cultivar of Phlox plant, botanically known as *Phlox paniculata*, and hereinafter referred to by the cultivar name Rubymine.

The new Phlox is a naturally-occurring whole plant mutation of the *Phlox paniculata* cultivar Bright Eye Elite, not patented. The new Phlox was discovered by the Inventor in a controlled environment in Den Hoorn, The Netherlands, within a population of plants of 'Bright Eye Elite' in 1998. The selection of this new Phlox was based on its unique variegated foliage. Plants of the cultivar Bright Eye Elite have solid green-colored foliage whereas plants of the new Phlox have variegated foliage.

Asexual reproduction of the new cultivar by vegetative cuttings taken at Den Hoorn, The Netherlands since 1999, has shown that the unique features of this new Phlox are stable and reproduced true to type in successive generations.

SUMMARY OF THE INVENTION

Plants of the cultivar Rubymine have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'Rubymine'. These characteristics in combination distinguish 'Rubymine' as a new and distinct cultivar:

1. Unique pale yellow and green variegated foliage.
2. Upright plant habit.
3. Numerous light pink and purple bi-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Phlox.

The photograph at the top of the first sheet comprises a side perspective view of a typical flowering stem of 'Rubymine'.

The photograph at the top of the second sheet comprises a close-up view of a typical inflorescence of 'Rubymine'.

The photograph at the bottom of the second sheet comprises a close-up view of the upper surface of mature and young leaves of 'Rubymine'.

DETAILED BOTANICAL DESCRIPTION

The following observations, measurements and values describe plants of the new cultivar grown in the field under outdoor conditions during the summer in Den Hoorn, The Netherlands. Plants used in the photographs and the detailed botanical description were about 30 weeks from planting rooted cuttings. Color references are made to The Royal Horticultural Society Colour Chart except where general terms of ordinary dictionary significance are used.

Botanical classification: *Phlox paniculata* cultivar Rubymine.

Parentage: Naturally-occurring whole plant mutation of *Phlox paniculata* cultivar Bright Eye Elite, not patented.

Propagation:
- *Type cutting.*—Vegetative cuttings.
- *Time to produce a rooted liner.*—About 30 days during the spring in Den Hoorn, The Netherlands.
- *Root description.*—Fine.

Plant description:
- *Form.*—Upright, conical.
- *Usage.*—Perennial garden plant.
- *Crop time.*—From cuttings, about 30 weeks are required to produce fully-grown flowering plants in 1.5-liter containers.
- *Plant height.*—About 80 cm.
- *Area of spread.*—About 30 cm.
- *Vigor.*—Moderately vigorous.
- *Branching habit.*—Freely basal branching; about four basal branches develop per plant.
- *Stems.*—Length: About 80 cm. Diameter: About 4 mm. Internode length: About 3 cm. Texture: Smooth. Color: 137A with random spots of anthocyanin, close to 183A to 183B.

*Foliage description.*—Leaves simple, opposite, generally symmetrical, durable and long persisting. Length: About 12.5 cm. Width: About 4 cm. Shape: Elliptic to narrowly elliptic. Apex: Acute. Base: Attenuate to slightly cordate. Margin: Entire. Texture, both surfaces: Leathery; somewhat rugose. Leaf margins of young leaves, pubescent. Venation pattern: Pinnate. Color: Variegated with irregular central green patterns surrounded by irregular pale yellow patterns extending towards margins. Young foliage, upper surface: Center, 137A; margins, 145A to 145B, with anthocyanin, 183A to 183B. Young foliage, lower surface: Center, 137A; margins, 182A. Mature foliage, upper surface: Center, 147A to 137A; interspersed between center and margins, random paler green, 147C to 147D, spots; margins, 11C. Mature foliage, lower surface: Center, 191A; margins, 11C. Venation, upper surface: 147A to 137A. Venation, lower surface: 143C. Petiole: Length: About 3 mm. Diameter: About 2.5 mm. Texture, both surfaces: Smooth. Color: Upper surface 147A to 137A. Lower surface: 143C.

Flower description:

*Flower type and habit.*—Single salverform light pink and purple bi-colored flowers arranged in upright panicles; flowers face upward and outward. Flowers not persistent.

*Natural flowering season.*—Flowering continuous during the summer from July to early September in Den Hoorn, The Netherlands.

*Quantity.*—Freely flowering with about 175 open flowers and flower buds per flowering stem over the entire flowering period.

*Fragrance.*—Moderate; pleasant sweet fragrance, typical of species.

*Flower longevity on the plant.*—About 6 days.

*Flower longevity as a cut flower.*—About 10 to 14 days.

*Flower buds, about two days before opening.*—Length: About 2.2 cm. Diameter: About 6 mm. Shape: Ovate. Color: 67A to slightly paler than 67A.

*Corolla.*—Arrangement: Five-parted, petals fused at base into a slender tube, salverform. Flower diameter: About 2.9 cm. Flower height: About 2 cm. Flower tube length: About 1.4 cm. Petal length from throat: About 1.4 cm. Petal width: About 1 cm. Petal shape: Beyond tube, flabellate. Petal apex: Rounded to broadly acute. Petal margin: Entire. Texture: Smooth, velvety; tube, sparsely covered with very short, less than 0.1 mm, whitish hairs. Petal color: When opening, upper surface: Close to 155D; towards base, 57C to 66C. When opening, lower surface: Paler than 66C to 66D; towards base, 66C to 66D. Opened flower, upper surface: 62C; towards base, 66B. Opened flower, lower surface: 68B. Throat: 66B. Tube: 68D.

*Calyx.*—Calyx length: About 1.1 cm. Calyx diameter: About 4 mm. Sepal arrangement: Five fused at base, campanulate. Sepal shape: Linear. Sepal apex: Acuminate. Sepal margin: Entire. Sepal texture, both surfaces: Smooth. Sepal color: Upper surface: 144C. Lower surface: 143B, anthocyanin towards apex, 183A.

*Peduncle.*—Angle: Upright to about 55° from stem. Strength: Moderate. Length: About 4 mm. Diameter: Less than 1 mm. Color: 141C to 143B.

*Reproductive organs.*—Stamens: Stamen quantity/arrangment: Five, adnate to corolla tube. Anther shape: Elliptic to ovate; basifixed. Anther length: About 1.5 mm. Anther color: 4C to 4D. Pollen amount: Moderate. Pollen color: Creamy white. Pistils: Pistil quantity: One. Pistil length: About 1.1 cm. Stigma shape: Three-parted. Stigma color: 157A to 157B. Style length: About 1 cm. Style color: 145D to 157A. Ovary color: 143C.

*Seed.*—Seed production has not been observed.

Disease/pest resistance: Resistance to pathogens or pests common to Phlox has not been observed.

It is claimed:

1. A new and distinct cultivar of Phlox plant named 'Rubymine', as illustrated and described.

* * * * *

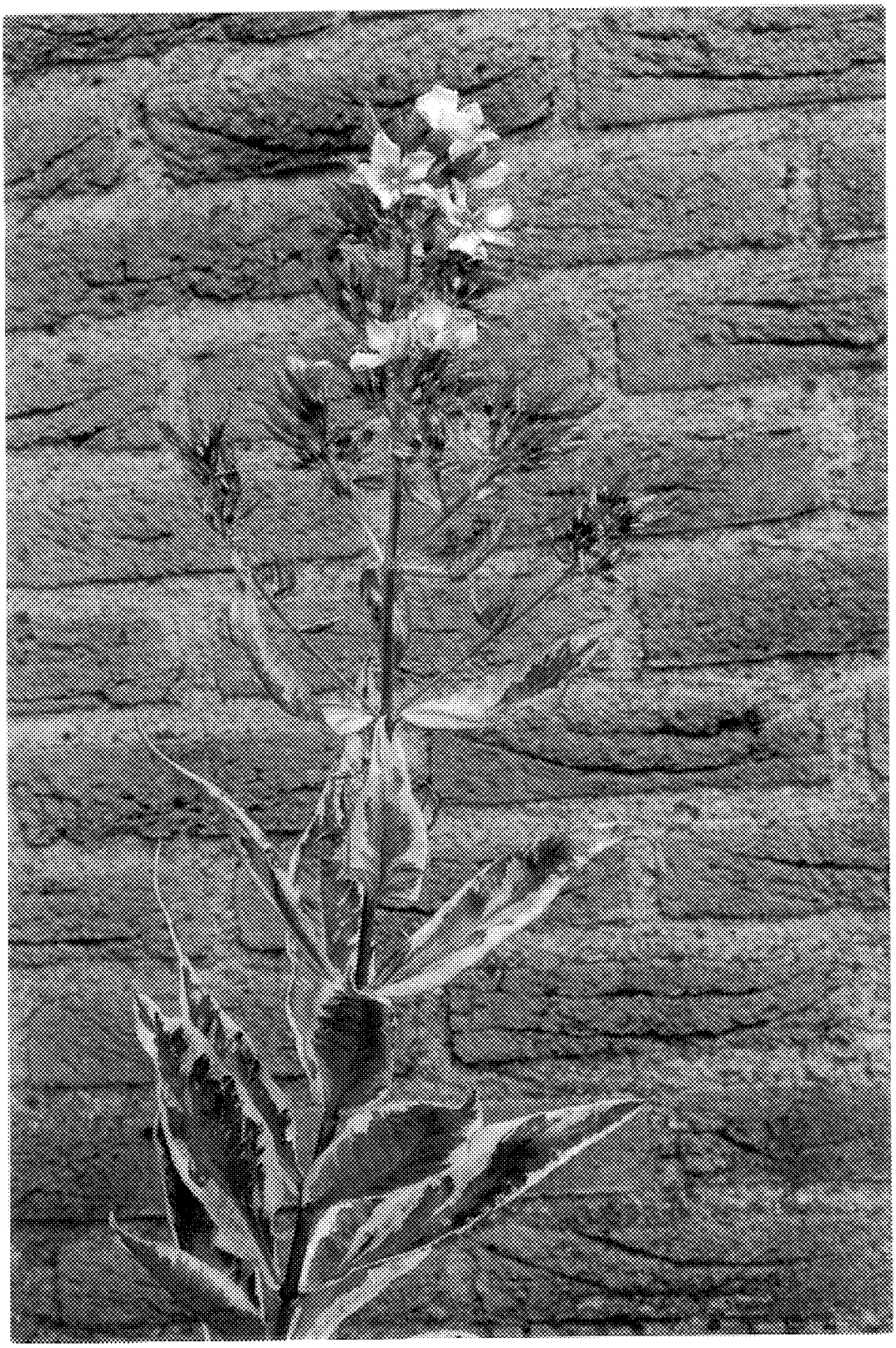

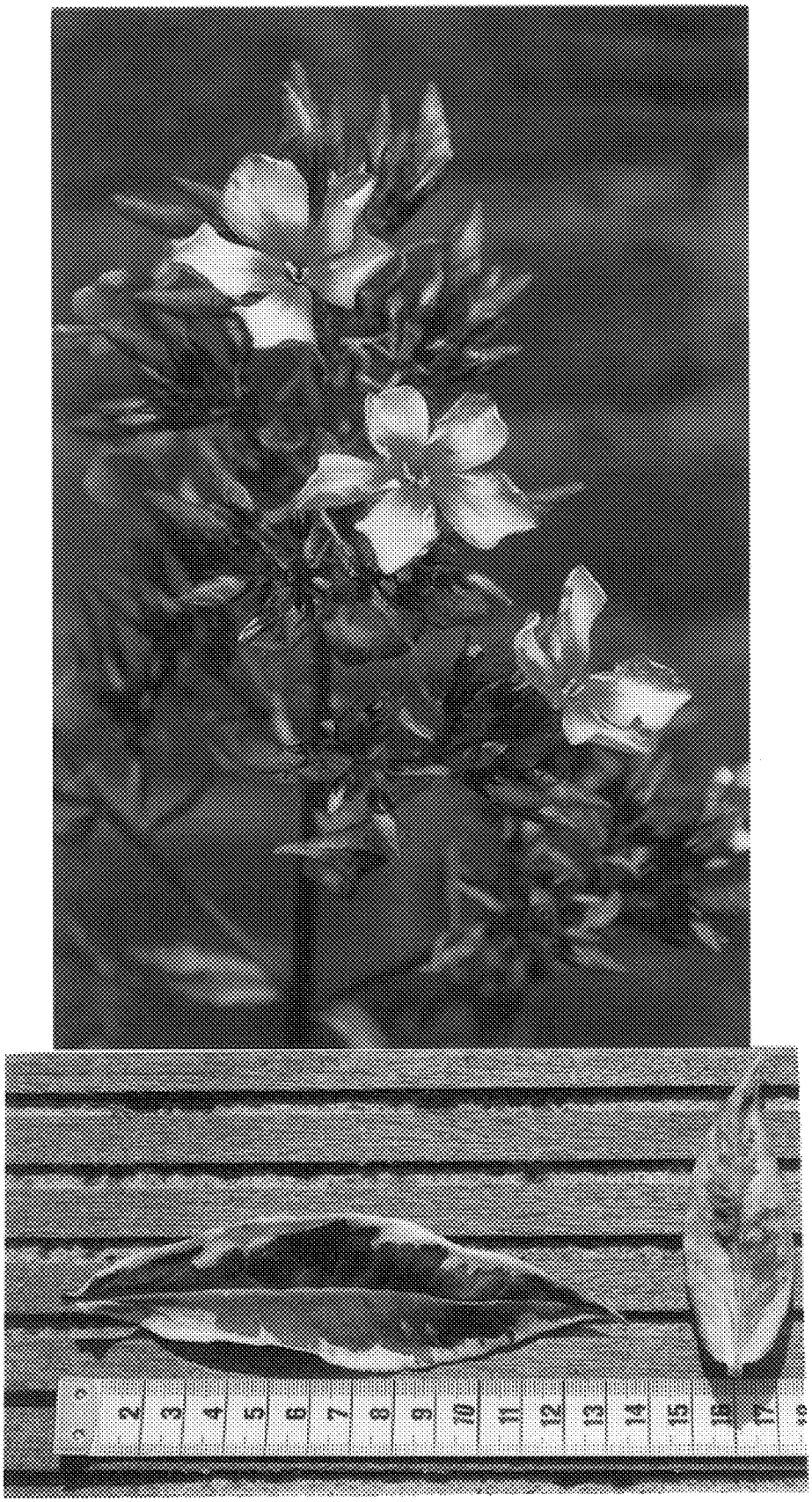
2
3
4
5
6
7
8
9
10
11
12
13
14
15
16
17
18